(12) United States Patent
Cao et al.

(10) Patent No.: US 10,558,670 B2
(45) Date of Patent: *Feb. 11, 2020

(54) SMART TUPLE CONDITION-BASED OPERATION PERFORMANCE

(71) Applicant: International Business Machines Corporation, Armonk, NY (US)

(72) Inventors: Bin Cao, Stanford, CA (US); Jessica R. Eidem, Rochester, MN (US); Brian R. Muras, Otsego, MN (US); Jingdong Sun, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 381 days.

This patent is subject to a terminal disclaimer.

(21) Appl. No.: 14/870,042

(22) Filed: Sep. 30, 2015

(65) Prior Publication Data

US 2017/0091283 A1    Mar. 30, 2017

(51) Int. Cl.
  *G06F 16/2455*  (2019.01)
  *G06F 19/00*    (2018.01)

(52) U.S. Cl.
  CPC ........ *G06F 16/24568* (2019.01); *G06F 19/32* (2013.01)

(58) Field of Classification Search
  CPC ............... G06F 17/30516; G06F 19/32; G06F 17/30545; G06F 16/24568; G06F 16/2471; G06F 8/41
  USPC ........................................................ 707/607
  See application file for complete search history.

(56) References Cited

U.S. PATENT DOCUMENTS

| | | | |
|---|---|---|---|
| 5,517,656 | A | 5/1996 | Shi |
| 5,937,401 | A | 8/1999 | Hillegas |
| 6,032,144 | A | 2/2000 | Srivastava et al. |
| 6,223,201 | B1 | 4/2001 | Reznak |
| 6,487,641 | B1 | 11/2002 | Cusson |
| 6,751,619 | B1 | 6/2004 | Rowstron et al. |
| 7,269,623 | B2 | 9/2007 | Neely, III et al. |
| 7,613,848 | B2 * | 11/2009 | Amini ............... H04L 29/06027 370/229 |
| 7,634,477 | B2 | 12/2009 | Hinshaw |

(Continued)

FOREIGN PATENT DOCUMENTS

EP    1860603 A2     11/2007
WO    2014182310 A1  11/2014

OTHER PUBLICATIONS

Ciancarini et al., "Parallel Symbolic Computing with the Shared Dataspace Coordination Model," 1994 Technical Report, 27 pages, Publisher University of Bologna © 1994.

(Continued)

*Primary Examiner* — Shahid A Alam
(74) *Attorney, Agent, or Firm* — Nolan M. Lawrence

(57) ABSTRACT

A stream application receives a stream of tuples to be processed by a plurality of processing elements operating on one or more compute nodes. Each processing element has one or more stream operators. The stream application assigns one or more processing cycles to one or more segments of software code. The segments of software code are embedded in one or more tuples of the stream of tuples. The stream application determines that a condition is met based on the processing cycles. The stream application performs an operation based on the processing cycles.

19 Claims, 5 Drawing Sheets

(56) References Cited

U.S. PATENT DOCUMENTS

| | | | |
|---|---|---|---|
| 7,644,110 B2* | 1/2010 | Nishizawa | G06F 17/30516 707/713 |
| 7,730,493 B2 | 6/2010 | Elms et al. | |
| 7,756,772 B1 | 7/2010 | Konopnicki | |
| 7,930,443 B1 | 4/2011 | Sullivan | |
| 8,051,069 B2 | 11/2011 | Johnson et al. | |
| 8,095,626 B2* | 1/2012 | Williams | G06F 9/44505 707/766 |
| 8,180,973 B1 | 5/2012 | Armangau et al. | |
| 8,578,390 B2 | 11/2013 | Dillow et al. | |
| 8,615,597 B2 | 12/2013 | Misra et al. | |
| 8,694,517 B2 | 4/2014 | Johnsen | |
| 8,719,415 B1 | 5/2014 | Sirota | |
| 8,762,297 B2* | 6/2014 | Chandramouli | G06N 99/005 706/12 |
| 8,788,482 B2 | 7/2014 | Hill | |
| 8,918,358 B2 | 12/2014 | Simitsis et al. | |
| 8,925,043 B2 | 12/2014 | Hildebrand | |
| 8,935,293 B2 | 1/2015 | Park et al. | |
| 8,972,405 B1* | 3/2015 | Chaulk | G06F 17/30194 707/737 |
| 8,996,486 B2 | 3/2015 | Hillis et al. | |
| 9,002,846 B2 | 4/2015 | Branson et al. | |
| 9,374,287 B2* | 6/2016 | Branson | H04L 47/125 709/224 |
| 9,411,636 B1 | 8/2016 | Ting et al. | |
| 9,436,736 B2* | 9/2016 | Branson | G06F 17/3053 707/713 |
| 9,703,839 B2* | 7/2017 | Branson | G06F 17/3053 709/204 |
| 2007/0156381 A1 | 7/2007 | Tisseau et al. | |
| 2008/0120337 A1 | 5/2008 | Fry | |
| 2009/0132544 A1 | 5/2009 | Hattori | |
| 2009/0225093 A1 | 9/2009 | Harper et al. | |
| 2009/0241127 A1 | 9/2009 | Reymann | |
| 2010/0073196 A1 | 3/2010 | Bogenberger | |
| 2010/0131565 A1 | 5/2010 | Weinberg | |
| 2010/0138438 A1 | 6/2010 | Torikai | |
| 2011/0099130 A1 | 4/2011 | Blumberg | |
| 2011/0178915 A1 | 7/2011 | Vinokour et al. | |
| 2011/0191759 A1 | 8/2011 | Andrade | |
| 2012/0096130 A1 | 4/2012 | Wei | |
| 2013/0031124 A1* | 1/2013 | Santosuosso | H04L 67/1097 707/769 |
| 2013/0085984 A1 | 4/2013 | Burger | |
| 2013/0179586 A1 | 7/2013 | Branson et al. | |
| 2013/0268560 A1* | 10/2013 | Pallares Lopez | G06F 9/5083 707/770 |
| 2013/0290394 A1 | 10/2013 | Branson et al. | |
| 2014/0024375 A1 | 1/2014 | Fitzpatrick | |
| 2014/0280895 A1 | 9/2014 | Branson et al. | |
| 2014/0304545 A1 | 10/2014 | Chen | |
| 2015/0032738 A1 | 1/2015 | Nachnani | |
| 2015/0071283 A1 | 3/2015 | Hammond et al. | |
| 2015/0193811 A1 | 7/2015 | Lei | |
| 2015/0331915 A1 | 11/2015 | Kravcik | |
| 2016/0188761 A1 | 6/2016 | Gil-Costa | |
| 2016/0303842 A1 | 10/2016 | Ponsolle et al. | |
| 2016/0306842 A1* | 10/2016 | Barsness | G06F 17/30303 707/692 |
| 2016/0321045 A1 | 11/2016 | Radigan | |
| 2017/0017553 A1 | 1/2017 | Peleg | |
| 2017/0091284 A1 | 3/2017 | Cao | |
| 2017/0091285 A1 | 3/2017 | Cao | |
| 2017/0091286 A1 | 3/2017 | Cao | |
| 2017/0091305 A1 | 3/2017 | Cao | |
| 2017/0124327 A1 | 5/2017 | Kumbhar et al. | |
| 2017/0223200 A1 | 8/2017 | Katano et al. | |

OTHER PUBLICATIONS

Ciancarini et al., "Jada: coordination and communication for Java agents," MOS '96 Selected Presentations and Invited Papers Second International Workshop on Mobile Object Systems—Towards the Programmable Internet, 16 pages, Springer-Verlag London, UK © 1997 ISBN: ISBN:3-540-62852-5.

Kielmann, T., "Object-Oriented Distributed Programming with Objective Linda," Proceedings of the First International Workshop on High Speed Networks and Open Distributed Platforms, Jun. 12-15, 1995, 15 pages, St. Petersburg, Russia.

Omicini et al., "From tuple spaces to tuple centres," Science of Computer Programming 41 (2001), pp. 277-294, Copyright 2001 Elsevier Science B.V. All rights reserved.

Tysowski et al., "JaCaL: An Implementation of Linda in Java," Proceedings of the Eleventh IASTED International Conference Parallel and Distributed Computing and Systems, Nov. 3-6, 1999, pp. 683-692 ISBN 0-88986-275-3.

Cammert et al., "A Cost-Based Approach to Adaptive Resource Management in Data Stream Systems," IEEE Transactions on Knowledge and Data Engineering, Feb. 2008, pp. 230-245, vol. 20, No. 2, Copyright 2008 IEEE.

Dittrich et al., "Data Redundancy and Duplicate Detection in Spatial Join Processing," 16th International Conference on Data Engineering, Feb. 29-Mar. 3, 2000, 12 pages DOI: 10.1109/ICDE.2000.839452.

Cao et al., "Smart Tuple Dynamic Grouping of Tuples," U.S. Appl. No. 14/870,041, filed Sep. 30, 2015.

Cao et al., "Smart Tuple Resource Estimation," U.S. Appl. No. 14/870,045, filed Sep. 30, 2015.

Cao et al., "Smart Tuple Stream Alteration," U.S. Appl. No. 14/870,052, filed Sep. 30, 2015.

List of IBM Patents or Patent Applications Treated as Related, Sep. 26, 2015, 2 pages.

Cao et al., "Smart Tuple Dynamic Grouping of Tuples," U.S. Appl. No. 14/934,292, filed Nov. 6, 2015.

List of IBM Patents or Patent Applications Treated as Related, Nov. 4, 2015, 2 pages.

* cited by examiner

SMART TUPLE CONDITION-BASED OPERATION PERFORMANCE

BACKGROUND

The present disclosure relates to stream computing, and more specifically, to performing an operation based upon a condition tested by a smart tuple in a smart stream computing environment.

Stream computing may be utilized to provide real-time analytic processing to large quantities of data. Stream computing may be used for scientific research purposes, such as weather forecasting and complex physics modelling. Stream computing may be used for commercial purposes, such as real-time inventory management and stock market tracking. Stream computing may be used for medical purposes, such as analyzing complex and interconnected functions of the human body. Stream computing may be used by end users to more immediately and accurately understand and contextualize large amounts of information.

SUMMARY

According to embodiments of the present disclosure, disclosed herein is a method for processing a stream of tuples. A stream application receives a stream of tuples to be processed by a plurality of processing elements operating on one or more compute nodes. Each processing element has one or more stream operators. The stream application assigns one or more processing cycles to one or more segments of software code. The segments of software code are embedded in one or more tuples of the stream of tuples. The stream application determines that a condition is met based on the processing cycles. The stream application performs an operations based on the processing cycles.

Also disclosed herein are embodiments of a system for processing a stream of tuples. The system includes a plurality of processing elements configured to receive a stream of tuples. Each processing element has one or more stream operators. The system also includes two or more processors. The system further includes a memory containing an application that causes at least one of the two or more processors to perform a method. A first processor embeds one or more tuples of the stream of tuples with one or more segments of software code. A second processor determines, based on the one or more segments of software code, that a condition is met. The second processor performs, based on the determination and the one or more segments of software code, an operation.

Also disclosed herein are embodiments of a computer program product for processing a stream of tuple. The computer program product includes a computer readable storage medium having program instructions executable by a plurality of processing elements operating on one or more compute nodes. Each processing element has one or more stream operators. A first compute node embeds one or more tuples of the stream of tuples with one or more segments of software code. A second compute node determines, based on the one or more segments of software code, that a condition is met. The second compute node performs, based on the determined condition and based on the one or more segments of software code, an operation.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
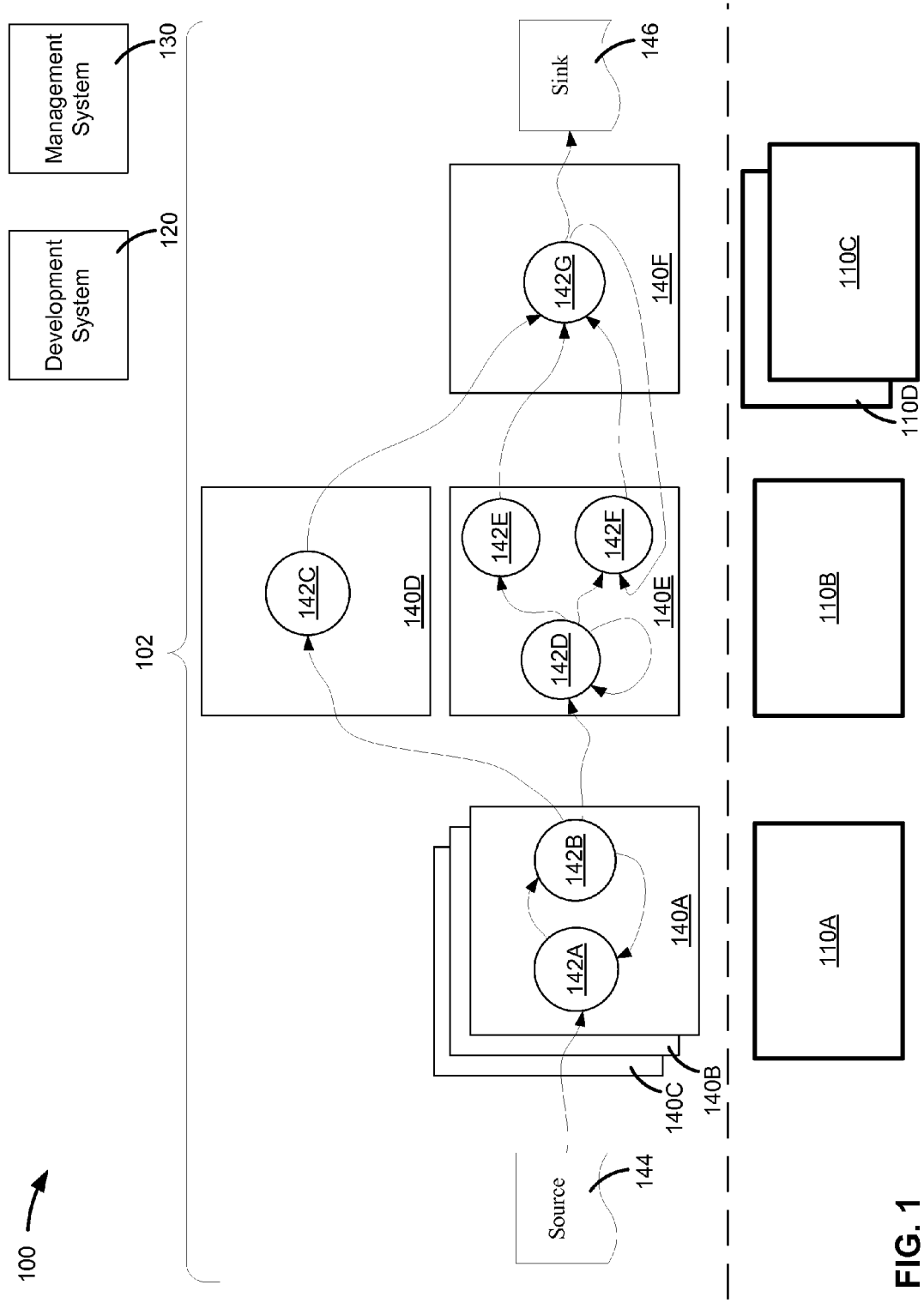
FIG. 1 depicts a stream computing application consistent with embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to stream computing, more particular aspects relate to performing an operation based upon a condition tested by a smart tuple in a smart streams computing environment. While the present disclosure is not necessarily limited to such applications, various aspects of the disclosure may be appreciated through a discussion of various examples using this context.

One of the primary uses of computing systems (alternatively, computer systems) is to collect available information, manipulate the collected information, and make decisions based on the manipulated information. Existing computer systems may operate on information through means of databases that allow users to determine what has happened and to make predictions for future results based on past events. These computer systems receive information from a variety of sources and then record the information into permanent databases. After the information has been recorded in the databases, the computing systems run algorithms on the information sometimes generating new information and then performing associated transformations on and storing of the new information—to make determinations and provide context to users.

The ability of these existing computer systems to analyze information and provide meaning to users may be insufficient in some situations. The ability of large organizations, such as corporations and governments, to make decisions based on information analysis may be impaired by the limited scope of the information available. In addition, the analysis may be of limited value because it relies on stored structural databases that may contain out-of-date information. This may lead to decisions that are of limited value or, in some cases, inaccurate. For example, a weather forecast service may be unable to accurately predict precipitation for a given region, or a stock brokerage firm may make an incorrect decision regarding a trend in trading of shares.

The analytical shortcomings of existing computer systems may be compounded by other factors. First, the world is becoming more instrumented, as previously unintelligent devices are now becoming intelligent devices. Intelligent devices may include devices that have historically been unable to provide analytical information but with the additions of sensors can now do so (e.g., automobiles that are now able to provide diagnostic information to their owners or manufacturers, thermostats that now communicate information about daily temperature fluctuations in homes to users via webpages). Second, these shortcomings may also be compounded by an increase in communication from information sources, as previously isolated devices are now becoming interconnected (e.g., appliances within homes communicate with each other and with power utilities to more efficiently utilize electricity). These new sources of information may provide volumes of not only isolated data points but also relationships between the newly intelligent devices.

A third compounding factor is that users of computing systems may desire continuous analysis of streams of information, while current methods of data acquisition may provide only an event-based approach of analyzing pre-recorded information. For example, an existing analytics package may receive a finite amount of data and, later, apply analysis to the data. This approach may not work when dealing with a continuous stream of data. A fourth compounding factor is that existing computer systems may have deficiencies in handling not only the volume of information but also in dealing with the unstructured nature of the information; for example, sensors, cameras, and other new data sources may provide no context or format, just raw information. The existing analytics methods of conventional computing systems may need to modify and rearrange this data in order to provide any kind of context for the raw information. The modifications and rearrangements may take time or resources that many existing computing systems may not be able to provide.

Yet another potential drawback is that existing computing systems may not provide scalable solutions to new users. The advent of smart and connected devices has provided new use-cases for analytics of continuous streams of information. Modern systems of large-scale data collection, however, may require significant user training and provide unintuitive interfaces. For example, a farmer may have each animal on a farm instrumented with sensors to monitor the health and location of the animals. The data from these sensors may enable the farmer to respond to ever-changing health conditions of the animals, but only if the sensor data is collected and transformed into a usable format to provide meaningful information to the farmer in real-time. The farmer may not have the money to provide training and resources to a technical expert to construct a large-scale analytics package, and the obtained information may be left used.

I. Stream Computing

Stream-based computing (e.g., within a stream application) may provide users with a way to obtain meaning from extremely large sets of information (big-data). Stream computing may provide users with the ability to analyze information as it is captured but before it reaches a final destination (e.g., data from sensors being transmitted to a flat file, records being collected from internet queries and being stored to a database). In some embodiments, stream computing may provide users with the ability to analyze a stream of information that is too large to be captured and placed into a final destination (e.g., sensor values from thousands of sensors that will be discarded after being measured could be utilized by a stream computing application to provide detailed analysis). Stream computing may provide the bandwidth to process big-data continuously and in real-time (e.g., generating context from tens of millions of records per second with low latency from record reception to provide meaningful action in microseconds). Stream computing may provide users with the ability to utilize familiar programmatic conventions to provide context to big-data (e.g., using a structured language to retrieve, format, and conditionally select a subset of information regarding millions of records as those records are generated, using conditional language to trigger an action every few milliseconds based on traditional program statements applied every hundred microseconds).

Information flowing through a stream application may be in the form of streams. A stream may be made up of one or more tuples. A tuple may be a sequence of one or more associated attributes in a relational format. The tuples may share characteristics of a classical relational database (e.g., a single tuple may be similar to a row in a relational database and the attributes of a tuple may be similar to the columns of the row). The tuples may have non-relational database relationships to other tuples of a stream application (e.g., individual values, key-value pairs, flat files, etc.). Tuples may include values in a variety of known computer formats (e.g., integer, float, Boolean, string, etc.). Tuples may contain attributes about themselves, such as metadata. As used herein, a stream, streams, or data stream may refer to a sequence of tuples flowing through a stream application. Generally, a stream may be considered a pseudo-infinite sequence of tuples.

FIG. 1 depicts a stream computing application (stream application) 100 consistent with embodiments of the present disclosure. The stream application 100 may be represented in the form of an operator graph 102. The operator graph 102 may visually represent to a user the flow of data through the stream application 100. The operator graph 102 may define how tuples are routed through the various components of the stream application 100 (e.g., an execution path). The stream application 100 may include one or more compute nodes 110A, 110B, 110C, and 110D (collectively, 110); a development system 120; a management system 130; one or more processing elements 140A, 140B, 140C, 140D, 140E, and 140F (collectively, 140); and one or more stream operators 142A, 142B, 142C, 142D, 142E, 142F, 142G (collectively, 142). The stream application 100 may receive information from one or more sources 144 and may output information to one or more sinks 146.

It should be appreciated that the stream application 100 depicted in FIG. 1 is for example purposes. Stream applications may vary in the number of compute nodes, processing elements, or stream operators. The stream application may also vary the roles and/or responsibilities performed by any of the components or may include other components not depicted. For example, some or all of the functionality of the development system 120 may be performed by the management system 130. In another example, the functionalities of the development system 120 and the management system 130 may be performed by a singular administrative system (not depicted). The administrative system may be configured to perform these tasks without deviation from the embodiments disclosed herein. In yet another example, the functionalities of the development system 120 and the management system 130 may be performed by a plurality of services (e.g., ten or more individual software programs each configured to perform a specific function).

Figure 5:
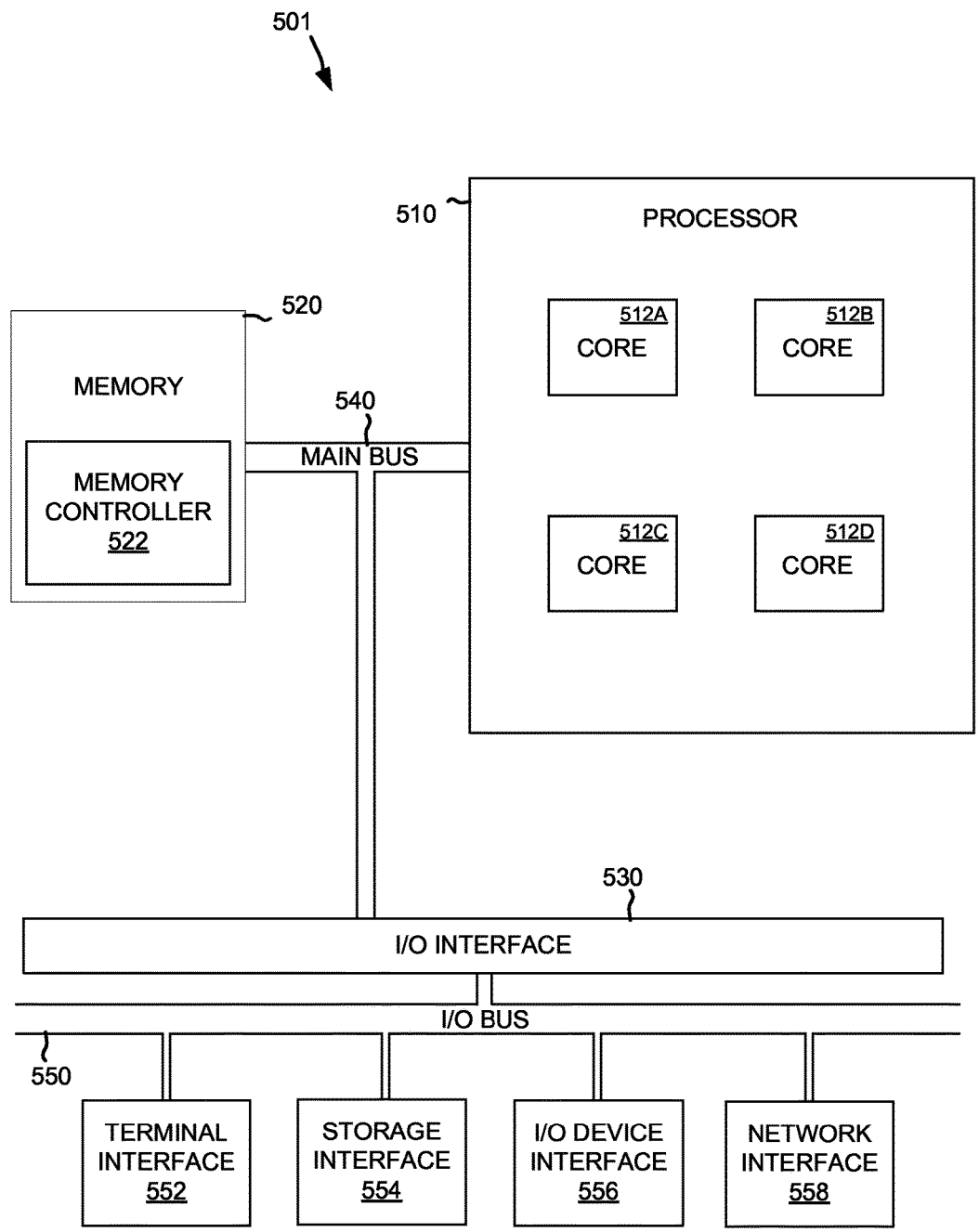
FIG. 5 depicts the representative major components of an example computer system that may be used, in accordance with embodiments of the present disclosure.

The compute nodes 110 may be computer systems and may each include the following components: a processor, a memory, and an input/output interface (herein I/O). Each compute node 110 may also include an operating system or a hypervisor. In some embodiments, the compute nodes 110 may perform operations for the development system 120, the management system 130, the processing elements 140, and/or the stream operators 142. The compute nodes 110 may be categorized as management hosts, application hosts, or mixed-use hosts. A management host may perform operations for the development system 120 and/or the management system 130. An application host may perform operations for the processing elements 140 and stream operators 142. A mixed-use host may perform operations of both a management host and an application host. FIG. 5 depicts a computer system that may be a compute node consistent with embodiments of the present disclosure.

A network (not depicted) may commutatively couple each of the nodes 110 together (e.g., a local area network, the Internet, etc.). For example, node 110A may communicate with nodes 110B, 110C, and 110D through the network. The computes nodes 110 may communicate with the network by way of the I/O. The network may include a variety of physical communication channels or links. The links may be wired, wireless, optical, or any other suitable media. The network may include a variety of network hardware and software for performing routing, switching, and other functions, such as routers, switches, or bridges. The nodes 110 may communicate through a variety of protocols (e.g., the internet protocol, the transmission control protocol, the file transfer protocol, the hypertext transfer protocol, etc.). In some embodiments, the nodes 110 may share the network with other hardware, software, or services (not depicted).

The development system 120 may provide a user with the ability to create a stream application that is targeted to process specific sets of data. The development system 120 may operate on a computer system (not depicted), such as the computer system depicted in FIG. 5. The development system 120 may operate on one or more of the compute nodes 110. The development system 120 may generate one or more configuration files that describes the stream computing application 100 (e.g., the processing elements 140, the stream operators 142, the sources 144, the sinks 146, the assignment of the aforementioned to the compute nodes 110, etc.). The development system 120 may receive requests from a user to generate the stream application 100. The development system 120 may receive requests from a user to generate other stream applications (not depicted). The development system 120 may communicate with the management system 130 to pass along the configuration on any stream applications it creates.

The development system 120 may generate the configuration by considering the performance characteristics of the software components (e.g., the processing elements 140, the stream operators 142, etc.) the hardware (e.g., the compute nodes 110, the network) and the data (e.g. the sources 144, the format of the tuples, etc.). In a first example, the development system 120 may determine that the overhead of running processing elements 140A, 140B, and 140C together on compute node 110A results in better performance than running them on separate compute nodes. The performance may be better because of a latency incurred by running processing elements 140A, 140B, and 140C across the network between compute nodes 110A and 110B. In a second example, the development system 120 may determine that the memory footprint of placing stream operators 142C, 142D, 142E, and 142F into a single processing element 140E is larger than the cache of a first processor in compute node 110B. To preserve memory space inside the cache of the first processor the development system 120 may decide to place only the stream operators 142D, 142E, and 142F into a single processing element 140E despite the inter-process communication latency of having two processing elements 140D and 140E.

In a third example of considering the performance characteristics, the development system 120 may identify a first operation (e.g., an operation being performed on processing element 140F on compute node 110C) that requires a larger amount of resources within the stream application 100. The development system 120 may assign a larger amount of resources (e.g., operating the processing element 140F on compute node 110D in addition to compute node 110C) to aid the performance of the first operation. The development system 120 may identify a second operation (e.g., an operation being performed on processing element 140A) that requires a smaller amount of resources within the stream application 100. The development system 120 may further determine that the stream application 100 may operate more efficiently through an increase in parallelization (e.g., more instances of processing element 140A). The development system 120 may create multiple instances of processing element 140A (e.g., processing elements 140B and 140C). The development system 120 may then assign processing elements 140A, 140B, and 140C to a single resource (e.g., compute node 110A). Lastly, the development system 120 may identify a third operation and fourth operation (e.g., operations being performed on processing elements 140D and 140E) that each require low levels of resources. The development system 120 may assign a smaller amount of resources to the two different operations (e.g., having them share the resources of compute node 110B rather than each operation being performed on its own compute node).

The development system 120 may include a compiler (not depicted) that compiles modules (e.g., processing elements 140, stream operators 142, etc.). The modules may be source code or other programmatic statements. The modules may be in the form of requests from a stream processing language (e.g., a computing language containing declarative statements allowing a user to state a specific subset from information formatted in a specific manner). The compiler may translate the modules into an object code (e.g., a machine code targeted to the specific instruction set architecture of the compute nodes 110). The compiler may translate the modules into an intermediary form (e.g., a virtual machine code). The compiler may be a just-in-time compiler that executes as part of an interpreter. In some embodiments, the compiler may be an optimizing compiler. In some embodiments, the compiler may perform peephole optimizations, local optimizations, loop optimizations, inter-procedural or whole-program optimizations, machine code optimizations, or any other optimizations that reduce the amount of time required to execute the object code, to reduce the amount of memory required to execute the object code, or both.

The management system 130 may monitor and administer the stream application 100. The management system 130 may operate on a computer system (not depicted), such as the computer system depicted in FIG. 5. The management system 130 may operate on one or more of the compute nodes 110. The management system 130 may also provide the operator graph 102 of the stream application 100. The management system 130 may host the services that make up the stream application 100 (e.g., services that monitor the health of the compute nodes 110, the performance of the processing elements 140 and stream operators 142, etc.). The management system 130 may receive requests from users (e.g., requests to authenticate and authorize users of the stream application 110, requests to view the information generated by the stream application, requests to view the operator graph 102, etc.).

The management system 130 may provide a user with the ability to create multiple instances of the stream application 100 configured by the development system 120. For example, if a second instance of the stream application 100 is required to perform the same processing, then the management system 130 may allocate a second set of compute nodes (not depicted) for performance of the second instance of the stream application. The management system 130 may also reassign the compute nodes 110 to relieve bottlenecks in the system. For example, as shown, processing elements 140D and 140E are executed by compute node 110B. Processing element 140F is executed by compute nodes 110C and 110D. In one situation, the stream application 100 may experience performance issues because processing elements 140D and 140E are not providing tuples to processing element 140F before processing element 140F enters an idle state. The management system 130 may detect these performance issues and may reassign resources from compute node 110D to execute a portion or all of processing element 140D, thereby reducing the workload on compute node 110B. The management system 130 may also perform operations of the operating systems of the compute nodes 110, such as the load balancing and resource allocation of the processing elements 140 and stream operators 142. By performing operations of the operating systems, the management system 130 may enable the stream application 100 to more efficiently use the available hardware resources and increase performance (e.g., by lowering the overhead of the operating systems and multiprocessing hardware of the compute nodes 110).

The processing elements 140 may perform the operations of the stream application 100. Each of the processing elements 140 may operate on one or more of the compute nodes 110. In some embodiments, a given processing element 140 may operate on a subset of a given compute node 110, such as a processor or a single core of processor of a compute node 110. In some embodiments, a given processing element 140 may operate on multiple compute nodes 110. The processing elements 140 may be generated by the development system 120. Each of the processing elements 140 may be in the form of a binary file and additionally library files (e.g., an executable file and associated libraries, a package file containing executable code and associate resources, etc.).

Each of processing elements 140 may include configuration information from the development system 120 or the management system 130 (e.g., the resources and conventions required by the relevant compute node 110 to which it has been assigned, the identity and credentials necessary to communicate with the sources 144 or sinks 146, the identity and credentials necessary to communicate with other processing elements, etc.). Each of the processing elements 140 may be configured by the development system 120 to run optimally upon one of the compute nodes 110. For example, processing elements 140A, 140B, and 140C may be compiled to run with optimizations recognized by an operating system running on compute node 110A. The processing elements 140A, 140B, and 140C may also be optimized for the particular hardware of compute node 110A (e.g., instruction set architecture, configured resources such as memory and processor, etc.).

Each of processing elements 140 may include one or more stream operators 142 that perform basic functions of the stream application 100. As streams of tuples flow through the processing elements 140, as directed by the operator graph 102, they pass from one stream operator to another. Multiple stream operators 142 within the same processing element 140 may benefit from architectural efficiencies (e.g., reduced cache missed, shared variables and logic, reduced memory swapping, etc.). The processing elements 140 and the stream operators 142 may utilize inter-process communication (e.g., network sockets, shared memory, message queues, message passing, semaphores, etc.). The processing elements 140 and the stream operators 142 may utilize different inter-process communication techniques depending on the configuration of the stream application 100. For example: stream operator 142A may use a semaphore to communicate with stream operator 142B; processing element 140A may use a message que to communicate with processing element 140C; and processing element 140B may use a network socket to communicate with processing element 140D.

The stream operators 142 may perform the basic logic and operations of the stream application 100 (e.g., processing tuples and passing processed tuples to other components of the stream application). By separating the logic that would conventionally occur within a single larger program into basic operations performed by the stream operators 142, the stream application 100 may provide greater scalability. For example, tens of compute nodes hosting hundreds of stream operators in a stream application may enable processing of millions of tuples per second. The logic may be created by the development system 120 before runtime of the stream application 100. In some embodiments, the sources 144 and the sinks 146 may also be stream operators 142. In some embodiments, the sources 144 and the sinks 146 may link multiple stream applications together (e.g., the sources 144 could be sinks for a second stream application and the sinks 146 could be sources for a third stream application). The stream operators 142 may be configured by the development system 120 to optimally perform the stream application 100 using the available compute nodes 110. The stream operators may 142 send and receive tuples from other stream operators. The stream operators 142 may receive tuples from the sources 144 and may send tuples to the sink 146.

The stream operators 142 may perform operations (e.g., conditional logic, iterative looping structures, type conversions, string formatting, etc.) upon the attributes of a tuple. In some embodiments, each stream operator 142 may perform only a very simple operation and may pass the updated tuple on to another stream operator in the stream application 100—simple stream operators may be more scalable and easier to parallelize. For example, stream operator 142B may receive a date value to a specific precision and may round the date value to a lower precision and pass the altered date value to stream operator 142D that may change the altered date value from a 24-hour format to a 12-hour format. A given stream operator 142 may not change anything about a tuple. The stream operators 142 may perform operations upon a tuple by adding new attributes or removing existing attributes.

The stream operators 142 may perform operations upon a stream of tuples by routing some tuples to a first stream operator and other tuples to a second stream operator (e.g., stream operator 142B sends some tuples to stream operator 142C and other tuples to stream operator 142D). The stream operators 142 may perform operations upon a stream of tuples by filtering some tuples (e.g., culling some tuples and passing on a subset of the stream to another stream operator). The stream operators 142 may also perform operations upon a stream of tuples by routing some of the stream to itself (e.g., stream operator 142D may perform a simple arithmetic operation and as part of its operation it may perform a logical loop and direct a subset of tuples to itself).

In some embodiments, a particular tuple output by a stream operator 142 or processing element 140 may not be considered to be the same tuple as a corresponding input tuple even if the input tuple is not changed by the stream operator or the processing element.

II. Smart Stream Computing

Stream computing may allow users to process big-data and provide advanced metrics upon that big-data continuously as it is being generated by a variety of sources. A stream application may provide stream computing by generating a configuration of one or more processing elements, each processing element containing one or more stream operators. Each processing element and/or stream operator of the stream application may process big-data by generating and modifying information in the form of tuples. Each tuple may have one or more attributes (e.g., the tuples may be analogous to rows and the attributes analogous to columns in a table).

The stream application may deploy an instance of the configuration to a set of hardware compute nodes. FIG. 5 depicts a computer system that may be a compute node consistent with embodiments of the present disclosure. The stream application may then administer the instance by adjusting the hardware to perform the stream application as it is configured, such as by load balancing the processing elements onto compute nodes, onto a portion of a given compute node, or across multiple compute nodes.

In some situations, a stream application may be largely a static big-data operating mechanism. Such a stream application once configured may not be changeable in the context it provides to a user. Further, in some situation, such a stream application performs certain logic in how it processes tuples. This logic once configured may not be updatable or changeable until a new stream application is compiled. Trying to provide an update to a processing element or stream operator of such a configured stream instance may be impractical because of the real-time continuous nature of stream applications and the information stream applications process. For example, any down-time, even in microseconds, may cause the stream application to not collect one or more tuples during the changeover from an originally configured processing element to an updated processing element. Missing a portion of the data may provide a partial or complete failure of the stream application and may result in the stream application being unable to provide users with context to big-data sources.

Choosing not to update the configuration of a stream application may also be undesirable because the configured logic may have faults or assumptions. For example, a user may be using an instance of a stream application to monitor weather from hundreds of weather sensors across many locations to better and more accurately guide and aim solar panels. If the user provided an error in the logic of the stream application or utilized an out-of-date set of metrics when the stream application was configured, the stream application may provide meaningless context. Such a misconfigured stream application may discard portions of meaningful tuples from the weather sensors, and without a way to alter the logic of the stream application while it is running, these tuples may be lost.

Associating a segment of code with one or more tuples may create a stream application with enhanced flexibility (smart stream application). A stream application may operate upon one or more tuples that contain attributes (e.g., tuples flow through pathways and are altered in some way by one or more stream operators and are sent along more pathways from those stream operators to other stream operators). A smart stream application may also have one or more code-embedded tuples (smart tuples)—a code-embedded tuple or smart tuple may also be referred to as an embedded tuple. The smart tuples may add further programming logic to a stream application by adding additional intelligence outside of the stream operators (e.g., adding processing power to the pathways by way of the tuples). The smart stream application may be able to dynamically modify the level of tuple processing power as resources allow (e.g., only a few tuples may be smart tuples during high usage, a large amount of tuples may be smart tuples during low usage, all or none of the tuples may be smart tuples, etc.). The smart stream application may alter the tuple processing power without upsetting the performance of the stream application (e.g., additional hardware may be added for processing smart tuples).

The smart tuples may have additional capabilities not found in normal tuples (e.g., know its own position in the stream application, communicate to other tuples, communicate with the administrative components of the stream application, communicate with components external to the stream application, etc.). The smart tuples may also provide additional flexibility to the stream application (e.g., changing the logic of the stream application by a smart tuple bypassing one or more processing elements and/or stream operators, adding increased logic during low volumes of data by providing additional operations through the smart tuple in between processing elements and/or stream operators). A smart stream application may also be updated by one or more smart tuples (e.g., a smart tuple may contain an update or patch).

In a first example, functionality for processing tuples within a first stream operator may be set to a specific formula. By utilizing smart tuples, a user could update the functionality through a smart tuple having an altered formula and an update script to enact the altered formula. The stream operator may receive the alteration to the formula from the update script and may begin processing tuples based on the altered formula. In a second example, a temporary change of functionality could occur through the use of multiple smart tuples. A second stream operator may perform a set action on a stream of tuples. Each of the multiple smart tuples may be encoded to perform an updated action on one tuple from the stream of tuples. The multiple smart tuples may also reroute the stream of tuples, thus bypassing the second stream operator. As long as the smart stream application provides processing of tuples to the smart tuples instead of the second stream operator the updated action may occur upon the stream of tuples. In a third example, a temporary addition of functionality could occur through the use of multiple smart tuples. A third stream operator may perform calculations and update attributes from a first subset of a stream of tuples. Each of the multiple smart tuples may be encoded to perform the calculations on a subset of the stream of tuples not updated by the third stream operator. As long as the smart stream application provides processing of tuples to the smart tuples in addition to the third stream operator an increased level of detail may occur upon the stream of tuples—more tuples from the stream of tuples may have updated attributes.

Figure 2:
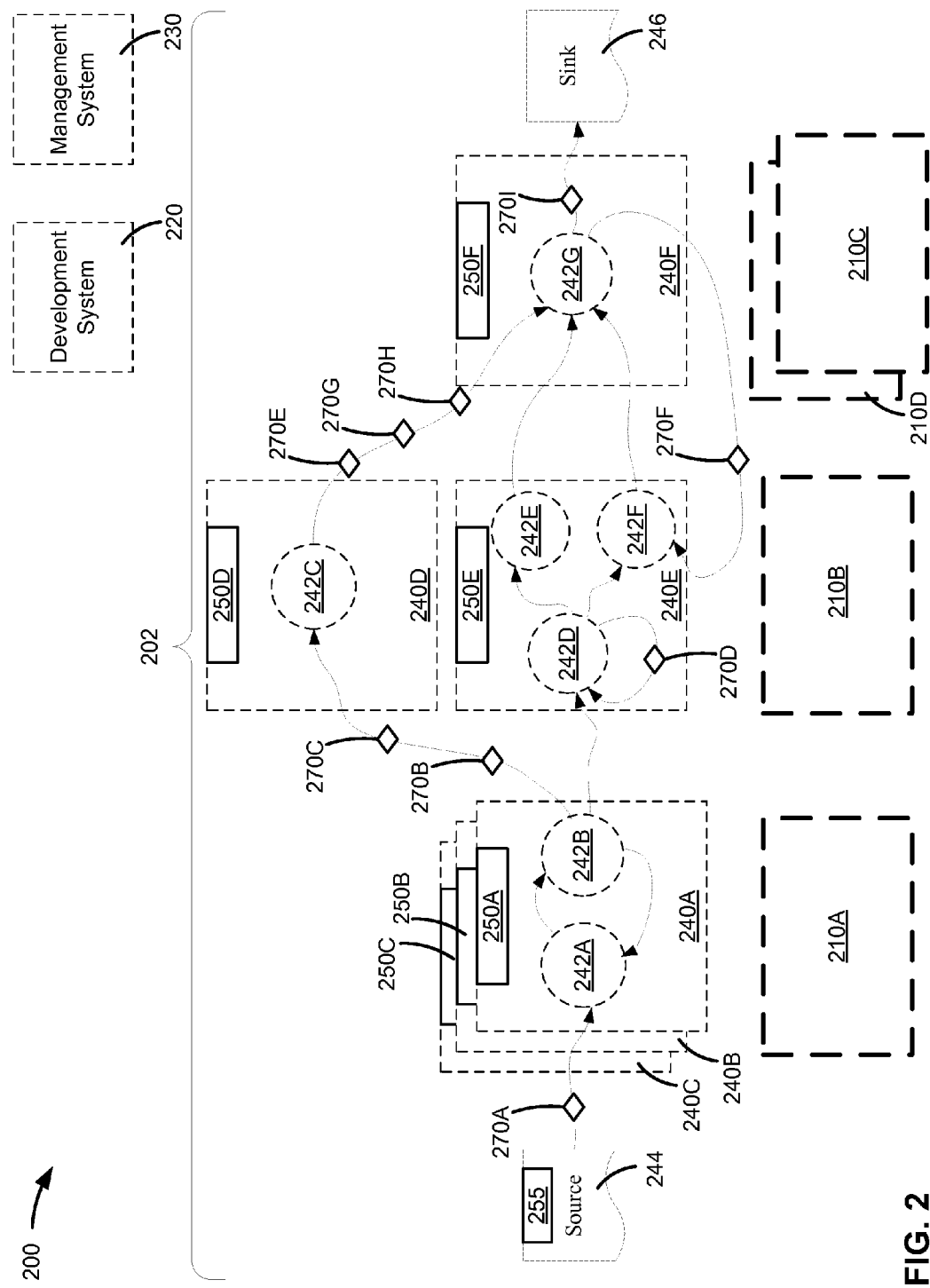
FIG. 2 depicts a smart stream application consistent with embodiments of the present disclosure.

FIG. 2 depicts a smart stream application 200 consistent with embodiments of the present disclosure. The smart stream application 200 may be represented in the form of an operator graph 202. The operator graph 202 may visually represent to a user the flow of data through the smart stream application 200. The operator graph 202 may define how tuples are routed through the various components of the smart stream application 200 (e.g., an execution path). The smart stream application 200 may include one or more compute nodes 210A, 210B, 210C, and 210D (collectively, 210); a development system 220; a management system 230; one or more processing elements 240A, 240B, 240C, 240D, 240E, and 240F (collectively, 240); and one or more stream operators 242A, 242B, 242C, 242D, 242E, 242F, 242G (collectively, 242). The smart stream application 200 may receive information from a source 244 and may output information to a sink 246. The source 244 and the sink 246 may be stream operators. The compute nodes 210 may be communicatively coupled to each other through a network (not depicted). The smart stream application 200 may also include one or more processing element tuple executors (PETEs) 250A, 250B, 250C, 250D, 250E, and 250F (collectively 250); and one or more stream operator tuple executors (SOTEs) 255. The functionality of a PETE could be replicated by one or more SOTEs (e.g., PETE 250E could be replicated by a SOTE within stream operators 242D, 242E, and 242F).

The compute nodes 210 may be one or more physical or virtual computers that are configured to enable execution of the other components of the smart stream application 200. FIG. 5 depicts a computer system that may be a compute node consistent with embodiments of the present disclosure. The development system 220 may enable the smart stream application to generate the operator graph 202 based on a request from the user. The development system 220 may receive from the user a request to perform some kind of structure-language query (e.g., select a subset of readings from hundreds of vitality sensors in a dozen hospitals based on a complex criteria continuously throughout a month, and, as the millions of readings in the subset are selected, format them in a certain arrangement, perform subtotaling and generate periodic notifications, etc.). The development system 220 may assess the available compute nodes 210 and generate the operator graph 202 (e.g., the layout and arrangement of the processing elements 240 and stream operators 242). The management system 230 may monitor the smart stream application 200 as it operates and provide management capabilities such as reassigning compute nodes 210 to alleviate bottlenecks.

The smart stream application 200 may be configured to process tuples (each tuple being an association of one or more attributes) collected from the source 244 and deposit the processed tuples in the sink 246. In detail, the source 244 may generate tuples that flow to the processing elements 240A, 240B, 240C. The processing elements 240A, 240B, and 240C may receive the tuples and generate a second and third set of tuples—then processing elements 240A, 240B, and 240C may send the second and third sets of tuples to processing elements 240D and 240E, respectively. The processing element 240D and may generate a fourth set of tuples from the second set of tuples and pass the fourth set of tuples onto processing element 240F. The processing element 240E may generate a fifth set of tuples from the third set of tuples and pass the fifth set of tuples onto processing element 240F. Finally processing element 240F may generate a sixth set of tuples and pass the sixth set of tuples onto the sink 246. In each of the processing elements 240 the stream operators 242 may perform the alterations to the tuples (e.g., adding or removing attributes, generating new attributes, determining the route of tuples, adding new tuples, removing existing tuples, etc.). In some embodiments, the stream operators 242 may pass tuples to each other within a given processing element 240 (e.g., stream operators 242A and 242B within processing element 240A).

The PETEs 250 and SOTEs 255 may be configured to enable the creation and processing of the smart tuples 270A, 270B, 270C, 270D, 270E, 270F, 270G, 270H, 270I (collectively, 270). The management system 230 may also be configured to enable the creation and processing of the smart tuples 270 in the smart stream application 200. In detail, the management system 230 may enable smart stream operation by sending a command to the source 244 along with one or more segments of code. The SOTE 255 may generate the smart tuples 270 by wrapping them with the segments of code (e.g., adding attributes to the tuples that contain a code object, adding attributes to the tuples that contain a link to a code object, etc.). The code objects may also be added to the compute nodes 210 such that they are accessible by processing elements 240 and stream operators 242. The management system 230 may also enable smart stream operation by sending a command to the processing elements 240.

The processing elements 240 in response to the management system 230 may instruct the PETEs 250 to detect smart tuples 270 and may provide access to processing cycles of the compute nodes 210 to the segments of code wrapped in the smart tuples 270. The PETEs 250 and SOTEs 255 may receive access to processing cycles periodically (e.g., every nanosecond, every three operations of a given stream operator 242, every ten operations of a given processing element 240, etc.). The PETEs and SOTEs may receive access to the processing cycles in another manner (e.g., before execution of a given stream operator 242, after execution of a given stream operator, etc.). The processing elements 240 and stream operators 242 may preserve the smart tuples 270 as they receive tuples, process the received tuples, and generate new tuples. For example, during the processing of tuples stream operator 242C may generate new tuples (e.g., perform some processing and create a new tuple based on the result). Smart tuple 270C may be processed by stream operator 242C upon entering processing element 240D. During generation of a new tuple based on smart tuple 270C, the stream operator may wrap the new tuple with the same segment of code that was wrapped with smart tuple 270C.

The management system 230 may be configured to disable the smart stream operation of the smart stream application 200. The management system 230 may disable smart stream operation by searching for each of the smart tuples 270 and unwrapping the segments of code (e.g., removing attributes from the tuples that contain a code object, removing attributes from the tuples that contain a link to a code object, etc.). In some embodiments, the management system 230 may disable smart stream operation by sending signals to the processing elements 240, the stream operators 242, and/or the source 244 to ignore the wrapped segments of code.

Figure 3:
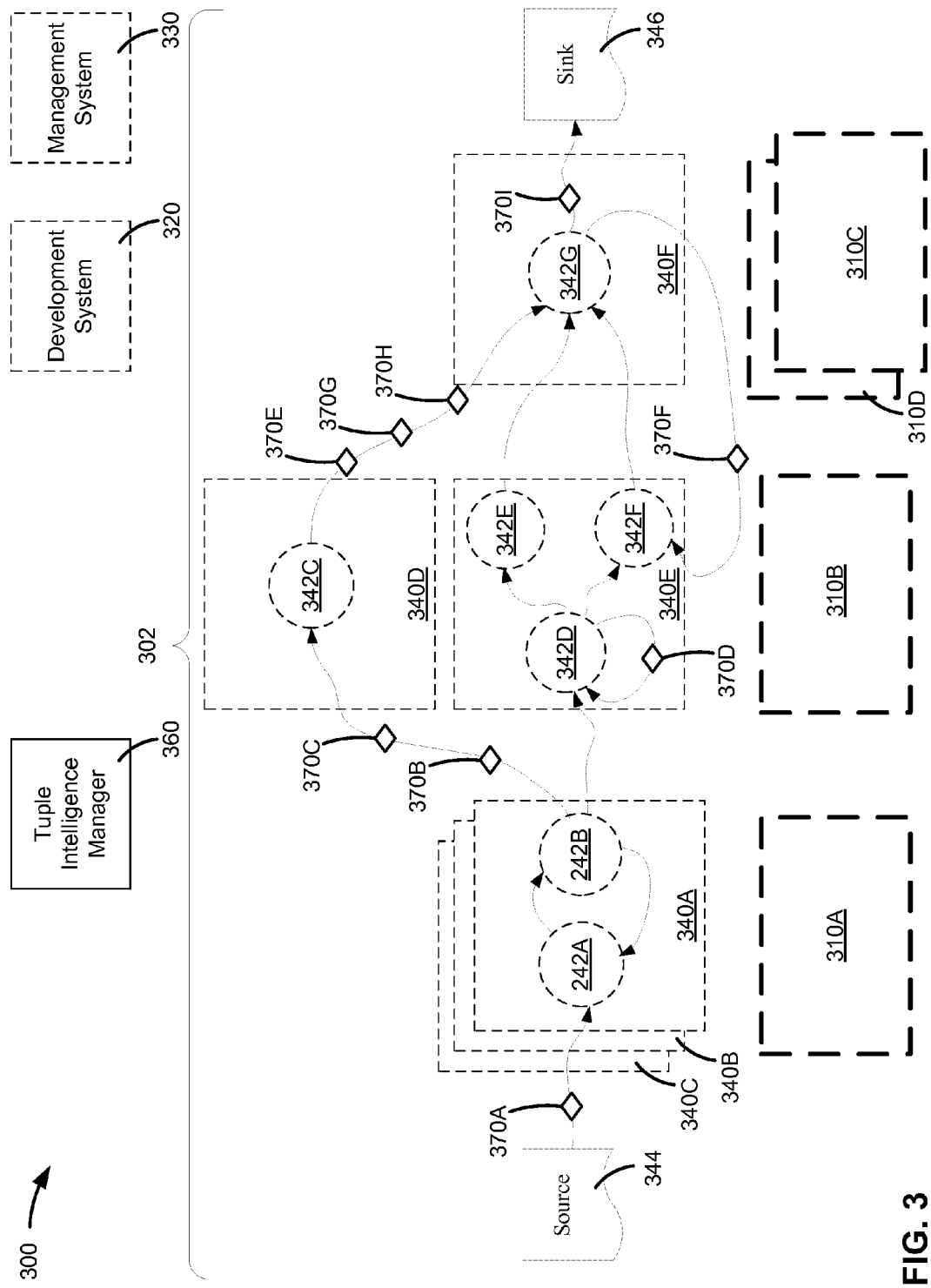
FIG. 3 depicts a stream application with smart stream capabilities consistent with embodiments of the present disclosure.

FIG. 3 depicts a stream application 300 with smart stream capabilities consistent with embodiments of the present disclosure. The stream application 300 may be represented in the form of an operator graph 302. The operator graph 302 may define how tuples are routed through the various components of the stream application 300 (e.g., an execution path). The stream application 300 may include one or more compute nodes 310A, 310B, 310C, and 310D (collectively, 310); a development system 320; a management system 330; one or more processing elements 340A, 340B, 340C, 340D, 340E, and 340F (collectively, 340); and one or more stream operators 342A, 342B, 342C, 342D, 342E, 342F, 342G (collectively, 342). The stream application 300 may receive information from a source 344 and may output information to a sink 346. The source 344 and the sink 346 may be stream operators. The compute nodes 310 may be communicatively coupled to each other through a network (not depicted). The stream application 300 may also include a tuple intelligence manager 360 (TIM). The TIM 360 may commutatively couple to the network and may be configured to interact with the other components of the stream application 300.

The compute nodes 310 may be one or more physical or virtual computers that are configured to enable execution of the other components of the stream application 300. FIG. 5 depicts a computer system that may be a compute node consistent with embodiments of the present disclosure. The development system 320 may enable the stream application to generate the operator graph 302 based on a request from the user. The development system 320 may receive from the user a request to perform some kind of structure-language query (e.g., select a subset of readings from hundreds of vitality sensors in a dozen hospitals based on a complex criteria continuously throughout a month, and, as the millions of readings in the subset are selected, format them in a certain arrangement, perform subtotaling and generate periodic notifications, etc.). The development system 320 may assess the available compute nodes 310 and generate the operator graph 302 (e.g., the layout and arrangement of the processing elements 340 and stream operators 342). The management system 330 may monitor the stream application 300 as it operates and provide management capabilities such as reassigning compute nodes 310 to alleviate bottlenecks.

The stream application 300 may be configured to process tuples (each tuple being an association of one or more attributes) collected from the source 344 and deposit the processed tuples in the sink 346. In detail, the source 344 may generate tuples that flow to the processing elements 340A, 340B, 340C. The processing elements 340A, 340B, and 340C may receive the tuples and generate a second and third set of tuples—then processing elements 340A, 340B, and 340C may send the second and third sets of tuples to processing elements 340D and 340E, respectively. The processing element 340D and may generate a fourth set of tuples from the second set of tuples and pass the fourth set of tuples onto processing element 340F. The processing element 340E may generate a fifth set of tuples from the third set of tuples and pass the fifth set of tuples onto processing element 340F. Finally processing element 340F may generate a sixth set of tuples and pass the sixth set of tuples onto the sink 346. In each of the processing elements 340 the stream operators 342 may perform the alterations to the tuples (e.g., adding or removing attributes, generating new attributes, determining the route of tuples, adding new tuples, removing existing tuples, etc.). In some embodiments, the stream operators 342 may pass tuples to each other within a given processing element 340 (e.g., stream operators 342A and 342B within processing element 340A).

The TIM 360 may be configured to enable the creation and processing of the smart tuples 370A, 370B, 370C, 370D, 370E, 370F, 370G, 370H, 370I (collectively, 370). In detail, the TIM 360 may enable smart stream operation by generating the smart tuples 370. The smart tuples 370 may be generated by wrapping them with the segments of code (e.g., adding attributes to the tuples that contain a code object, adding attributes to the tuples that contain a link to a code object, etc.). The code objects may also be added to the compute nodes 310 such that they are accessible by processing elements 340 and stream operators 342.

The TIM 360 may provide access to processing cycles of the compute nodes 310 to the segments of code wrapped in the smart tuples 370. In some embodiments, the TIM 360 may enable smart stream operation by providing access to processing cycles of additional computing systems (not depicted). The TIM 360 may provide access to processing cycles periodically (e.g., every nanosecond, every three operations of a given stream operator 342, every ten operations of a given processing element 340, etc.). The TIM 360 may provide access to the processing cycles in another manner (e.g., before execution of a given stream operator 342, after execution of a given stream operator, etc.).

The TIM 360 may preserve the order of tuples in the stream application 300. In detail, while the TIM 360 is providing a given smart tuple 370 access to processing cycles, a given processing element 340 and/or stream operator 342 may be preparing to process the given smart tuple. The TIM 360 may prevent the given processing element 340 and/or stream operator 342 from processing the given smart tuple 370 by issuing a wait command to the given processing element and/or stream operator (either directly or through a request to the management system 330). In response to the wait command the given processing element 340 and/or stream operator 342 may pause operation until the given smart tuple 370 finishes.

The processing elements 340 and stream operators 342 may preserve the smart tuples 370 as they receive tuples, process the received tuples, and generate new tuples. For example, during the processing of tuples stream operator 342C may generate new tuples (e.g., perform some processing and create a new tuple based on the result). Smart tuple 370C may be processed by stream operator 342C upon entering processing element 340D. During generation of a new tuple based on smart tuple 370C, the stream operator may wrap the new tuple with the same segment of code that was wrapped with smart tuple 370C. In some embodiments, the TIM 360 may monitor the stream operators 342 and the processing elements 340 and may preserve the smart tuples 370 as new tuples are generated.

The TIM 360 may be configured to disable the smart stream operation of the stream application 300. The TIM 360 may disable smart stream operation by searching for each of the smart tuples 370 and unwrapping the segments of code (e.g., removing attributes from the tuples that contain a code object, removing attributes from the tuples that contain a link to a code object, etc.). In some embodiments, the TIM 360 may disable smart stream operation by no longer providing the segments of code wrapped in the smart tuples 370 with access to processing cycles of the compute nodes 310. In some embodiments, the TIM 360 may disable smart stream operation by no longer providing access to processing cycles of additional computing systems (not depicted).

III. Tuple Trigger

Figure 4:
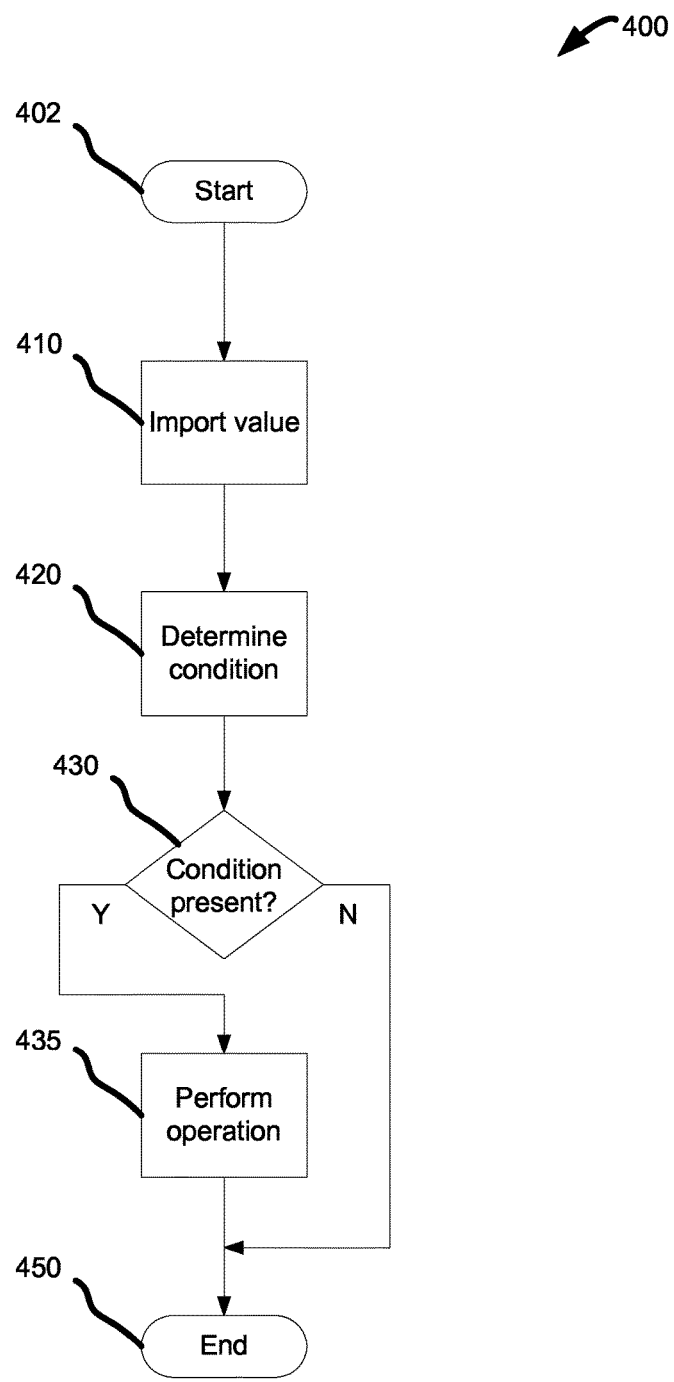
FIG. 4 depicts an example method for a smart tuple to conditionally perform an operation consistent with embodiments of the present disclosure.

FIG. 4 depicts an example method 400 for a smart tuple to conditionally perform an operation consistent with embodiments of the present disclosure. Method 400 may be executed by one or more smart tuples in a smart stream application to perform operations in response to the presence of a condition (e.g., activating a trigger in response to a condition). Method 400 may perform operations in addition to those depicted in FIG. 4. Method 400 may be executed by a given smart tuple during access to processing cycles from a compute node or other computer system. Thus, the stream application or one or more compute nodes providing processor, memory, and input/output to the stream application may also be executing method 400.

From start 402, a smart tuple may retrieve a relevant value at 410. The smart tuple may retrieve a relevant value at 410 by utilizing a network of the smart stream application. The value may relate to the smart tuple (e.g., a value contained in one of the attributes of the smart tuple, the position of the smart tuple within the smart stream application, etc.) The value may relate to one or more other tuples (e.g., a value contained in an attribute of another tuple, the presence of a tuple, the location of a tuple, etc.). The value may relate to a component of the stream application (e.g., a value of a management system, a value of a source, the status of a stream operator, the status of a processing element, the status of a network utilized by the stream application, etc.). The value may relate to information outside of the stream application (e.g., retrieving a temperature value from a website on the Internet). For example, the status of a stream operator may relate to its availability, such as the latency in response time from a ping request. In a second example, the status of a processing element may relate to the resources a compute node allocates during the processing of tuples (e.g., the number of processing cycles used by a processing element, the kilobytes of memory used by a processing element, etc.).

The smart tuple may determine if the value meets a condition at 420. The condition may include one or more criteria. The determination of the condition may be done by comparing the value to a single criterion, such as verifying if an attribute of the smart tuple is equal to '42'. The determination of the condition may be done by comparing the value to a range of values, such as verifying if an attribute is greater than '20' and less than '32.5'. The determination of the condition may be done by verifying that a value is present (e.g., ensuring a value from a processing element is not null). The condition may be that a particular stream operator responds to a ping. In some embodiments, the determination of the condition may be done by comparing multiple values to multiple criteria (e.g., verifying a first value is equal to '12.7' and a second value is not null).

If the condition is present, at 430, the smart tuple may perform an operation at 435. In embodiments where the condition includes multiple criteria, the condition may not be present, at 430, unless all criteria are met. The operation may be activating a trigger, such as generating a notification. The operation may be setting a value such as changing an attribute of the smart tuple. The operation may be communicating a message to a management system of the smart stream application. If the condition is not present, at 430, method 400 may end at 450.

For example, a smart tuple executing method 400 may check an operation of a stream operator. The stream operator may be in a stalled state and unresponsive to the administrative systems of the stream application. The smart tuple may obtain an operating status of the stream operator and determine from the operating status a network connectivity issue. The smart tuple may determine that the condition of the stream operator is that it is processing tuples but has lost connectivity to parts of the network that connect it to the administrative systems of the stream application. Based on the network connectivity issue the stream operator may transmit a copy of the operating status and an identifier of the stream operator to one or more of the administrative systems of the stream application.

FIG. 5 depicts the representative major components of an example computer system 501 that may be used, in accordance with embodiments of the present disclosure. It is appreciated that individual components may vary in complexity, number, type, and\or configuration. The particular examples disclosed are for example purposes only and are not necessarily the only such variations. The computer system 501 may comprise a processor 510, memory 520, an input/output interface (herein I/O or I/O interface) 530, and a main bus 540. The main bus 540 may provide communication pathways for the other components of the computer system 501. In some embodiments, the main bus 540 may connect to other components such as a specialized digital signal processor (not depicted).

The processor 510 of the computer system 501 may be comprised of one or more cores 512A, 512B, 512C, 512D (collectively 512). The processor 510 may additionally include one or more memory buffers or caches (not depicted) that provide temporary storage of instructions and data for the cores 512. The cores 512 may perform instructions on input provided from the caches or from the memory 520 and output the result to caches or the memory. The cores 512 may be comprised of one or more circuits configured to perform one or methods consistent with embodiments of the present disclosure. In some embodiments, the computer system 501 may contain multiple processors 510. In some embodiments, the computer system 501 may be a single processor 510 with a singular core 512.

The memory 520 of the computer system 501 may include a memory controller 522. In some embodiments, the memory 520 may comprise a random-access semiconductor memory, storage device, or storage medium (either volatile or non-volatile) for storing data and programs. In some embodiments, the memory may be in the form of modules (e.g., dual in-line memory modules). The memory controller 522 may communicate with the processor 510, facilitating storage and retrieval of information in the memory 520. The memory controller 522 may communicate with the I/O interface 530, facilitating storage and retrieval of input or output in the memory 520.

The I/O interface 530 may comprise an I/O bus 550, a terminal interface 552, a storage interface 554, an I/O device interface 556, and a network interface 558. The I/O interface 530 may connect the main bus 540 to the I/O bus 550. The I/O interface 530 may direct instructions and data from the processor 510 and memory 520 to the various interfaces of the I/O bus 550. The I/O interface 530 may also direct instructions and data from the various interfaces of the I/O bus 550 to the processor 510 and memory 520. The various interfaces may include the terminal interface 552, the storage interface 554, the I/O device interface 556, and the network interface 558. In some embodiments, the various interfaces may include a subset of the aforementioned interfaces (e.g., an embedded computer system in an industrial application may not include the terminal interface 552 and the storage interface 554).

Logic modules throughout the computer system 501—including but not limited to the memory 520, the processor 510, and the I/O interface 530—may communicate failures and changes to one or more components to a hypervisor or operating system (not depicted). The hypervisor or the operating system may allocate the various resources available in the computer system 501 and track the location of data in memory 520 and of processes assigned to various cores 512. In embodiments that combine or rearrange elements, aspects and capabilities of the logic modules may be combined or redistributed. These variations would be apparent to one skilled in the art.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method for processing a stream of tuples, the stream of tuples located in a stream-based computing environment designed to process big-data continuously and in real-time, the method comprising:
   receiving, by a stream application, a stream of tuples to be processed by a plurality of processing elements operating on one or more hardware compute nodes of the stream application, the tuples of the big-data set being processed before being recorded into a final destination, wherein at least one tuple of the stream of tuples contains one or more embedded segments of software code, wherein the stream application utilizes programmatic conventions to provide context to big-data using a structured language, wherein the programmatic conventions select a subset of information regarding millions of records as those records are generated, and wherein the stream application triggers actions every few milliseconds based on traditional program statements applied every hundred microseconds;
   assigning, one or more processing cycles to the one or more segments of software code embedded in the at least one tuple of the stream of tuples;
   determining, by the one or more processing cycles, a condition is met; and
   performing, based on the determined condition and by the one or more processing cycles, an operation on the stream application.

2. The method of claim 1, wherein the condition is based on the processing elements of the stream application.

3. The method of claim 2, wherein the condition is selected from the group consisting of availability of a given processing element, activity of a given processing element, activity of a given stream operator, latency of a given processing element, and an association between the compute nodes and the processing elements.

4. The method of claim 1, wherein the condition includes two or more criteria, and wherein the determining the condition is met includes determining the two or more criteria.

5. The method of claim 1, wherein the condition is based on the stream of tuples to be processed by the plurality of processing elements.

6. The method of claim 1, wherein the condition is based on the one or more embedded tuples.

7. The method of claim 1 further comprising the following:
   transmitting, by the one or more processing cycles, a notification of the performed operation to a user of the stream application.

8. The method of claim 1 further comprising the following:
   transmitting, by the one or more processing cycles, a notification of the performed operation to an application other than the stream application.

9. The method of claim 1 wherein the stream application embeds the one or more tuples of the stream of tuples with the one or more segments of software code.

10. The method of claim 1, wherein the one or more processing cycles are from a computer outside of the stream application.

11. A system for processing a stream of tuples, the stream of tuples located in a stream-based computing environment designed to process big-data continuously and in real-time, the system comprising:
   a plurality of processing elements configured to receive a stream of tuples, the tuples of the big-data set being processed before being recorded into a final destination, each processing element having one or more stream operators;
   two or more processors; and
   a memory containing an application that, when executed, causes at least one of the two or more processors to perform a method comprising:
      embedding, by a first processor, at least one tuple of the stream of tuples with one or more segments of software code, wherein the stream application utilizes programmatic conventions to provide context to big-data using a structured language, wherein the programmatic conventions select a subset of information regarding millions of records as those records are generated, and wherein the stream application triggers actions every few milliseconds based on traditional program statements applied every hundred microseconds;
      determining, by a second processor and based on the one or more segments of software code embedded within the at least one tuple, a condition is met; and
      performing, by the second processor and based on the determined condition and based on the one or more segments of software code embedded within the at least one tuple, an operation.

12. The system of claim 11, wherein the first processor and the second processor are the same processor.

13. The system of claim 11, wherein the condition includes two or more criteria, and wherein the determining the condition is met includes determining the two or more criteria.

14. The system of claim 11, wherein the condition is based on the stream of tuples to be processed by the plurality of processing elements.

15. The system of claim 11, wherein the condition is based on the processing elements of the stream application.

16. A computer program product for processing a stream of tuples, the stream of tuples located in a stream-based computing environment designed to process big-data continuously and in real-time, the computer program product comprising a computer readable storage medium having program instructions embodied therewith, the program instructions executable by a processor, the program instructions cause the processor to perform a method comprising:
   receiving, by a stream application, a stream of tuples including a plurality of data tuples embedded with non-software data and at least one software tuple embedded with segments of software code, wherein the non-software data is processed by software of stream operators operating on a portion of processing cycles of hardware of compute nodes assigned to the stream application, the tuples of the big-data set being processed before being recorded into a final destination, wherein the stream application utilizes programmatic conventions to provide context to big-data using a structured language, wherein the programmatic conventions select a subset of information regarding millions of records as those records are generated, and wherein the stream application triggers actions every few milliseconds based on traditional program statements applied every hundred microseconds;
   assigning, by the stream application, a second portion of the hardware processing cycles to each embedded segment of software code of the at least one software tuple such that the at least one software tuple operates outside of the stream operators;

determining, by the stream application and based on the second portion of hardware processing cycles, a condition is met; and performing, by the stream application and based on the second portion of hardware processing cycles and based on the determined condition, an operation.

17. The computer program product of claim 16, wherein the condition is based on the stream of tuples to be processed by the plurality of processing elements.

18. The computer program product of claim 16, wherein the program instructions further comprise the following:
   transmitting a notification of the performed operation to a user.

19. The computer program product of claim 16, wherein the program instructions further comprise the following:
   transmitting a notification of the performed operation to another application.

\* \* \* \* \*